United States Patent [19]
Anderson

[11] 4,301,798
[45] Nov. 24, 1981

[54] VAGINAL SYRINGE

[76] Inventor: Roy A. Anderson, 4554 N. Malden St., Chicago, Ill. 60640

[21] Appl. No.: 111,545

[22] Filed: Jan. 14, 1980

[51] Int. Cl.³ ............................................. A61M 3/00
[52] U.S. Cl. .................................................. 128/239
[58] Field of Search ............... 128/239, 251, 232, 224

[56] References Cited

U.S. PATENT DOCUMENTS

| | | | |
|---|---|---|---|
| 1,763,079 | 6/1930 | Zacsek | 128/239 |
| 2,034,926 | 3/1936 | Smith | 128/239 |

FOREIGN PATENT DOCUMENTS 49893  3/1930  Norway .............................. 128/239

*Primary Examiner*—John D. Yasko

*Attorney, Agent, or Firm*—Hill, Van Santen, Steadman, Chiara & Simpson

[57] ABSTRACT

A vaginal syringe comprising an elongated body of a size to be partially inserted, when in use, in the vaginal canal with the body being provided with a fluid inlet in its proximal end portion and a fluid outlet in its distal end portion and also having a fluid discharge inlet which is so disposed that it will be positioned in the vaginal canal when said syringe is in use, and a discharge outlet in the proximate end portion which discharge outlet is so disposed that it will be positioned exteriorly of such a vaginal canal when in use. The body having two independent passageways therein, one of which connects a fluid inlet and outlet for the flow of liquid from the exterior into such a vaginal canal and the other of which connects said discharge inlet and said discharge outlet for the flow of liquid from the interior of such vaginal canal to the exterior thereof.

4 Claims, 8 Drawing Figures

U.S. Patent  Nov. 24, 1981  4,301,798
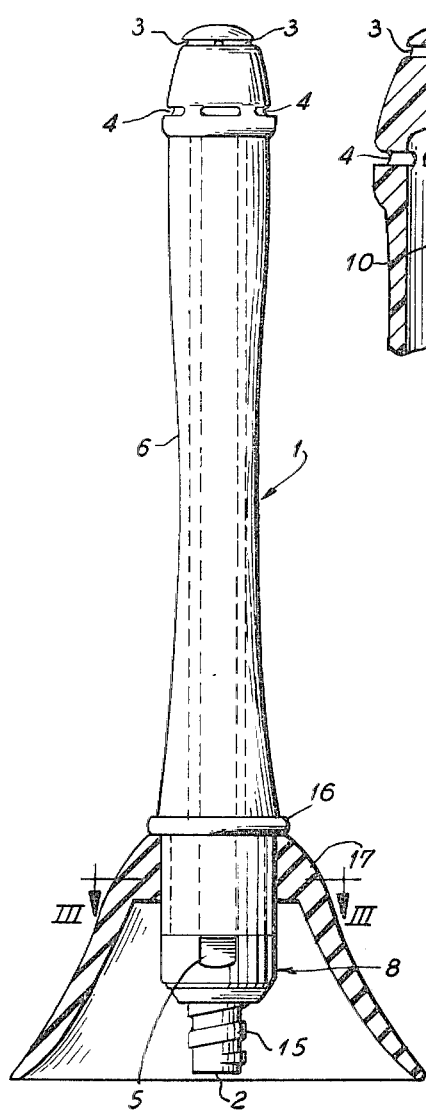
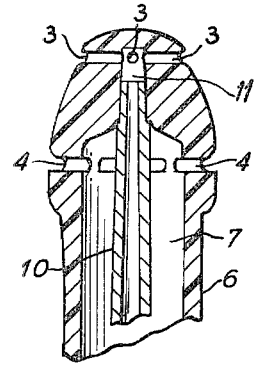
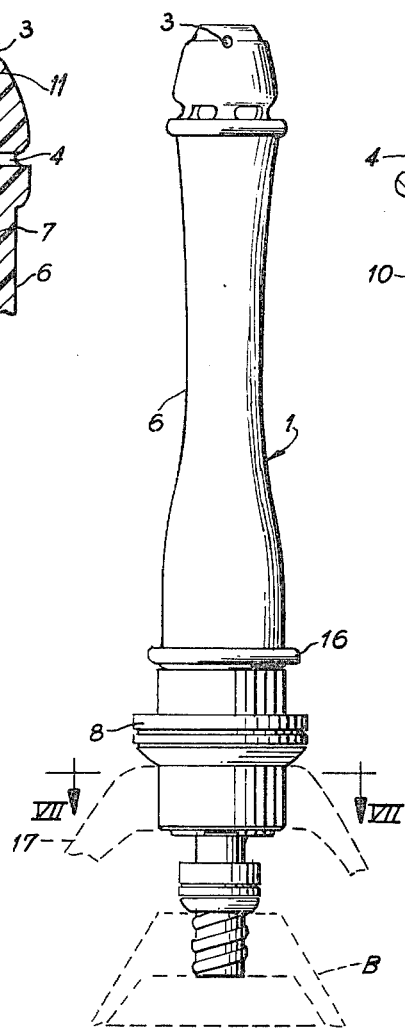
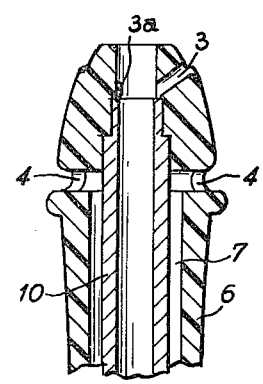
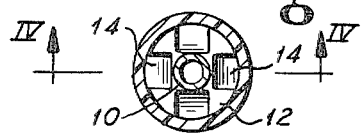
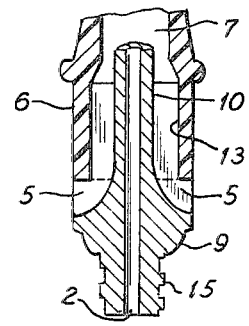
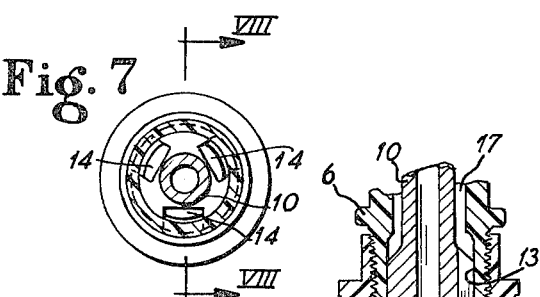
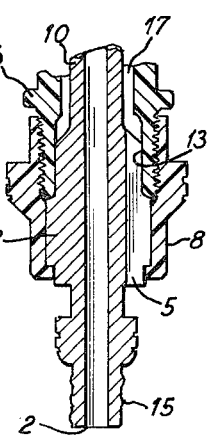

VAGINAL SYRINGE

BACKGROUND OF THE INVENTION

The present invention is directed to a vaginal irrigation syringe for use in connection with feminine hygiene.

Numerous devices have been designed for this purpose over the years, of which the following are typical.

U.S. Pat. No. 2,888,925 illustrates a typical structure in which a nozzle member is extended through a hollow ceramic body which is adapted to form the proximal end of the structure for sealing engagement with the vaginal orifice, and is provided with openings for the passage of liquid discharged from the nozzle into the hollow body, from which it may be discharged to the exterior, U.S. Pat. No. 1,481,989 illustrates a somewhat similar structure provided with additional means for extending and retracting the tubular nozzle member with respect to a body member through which it extends. Again, the sealing member is provided with apertures therein for the flow of liquid, discharged by the nozzle, from the body cavity and to the exterior.

U.S. Pat. No. 826,6855 illustrates a medical irrigator having a bulb structure which is provided with a tapering portion terminating at its small end in an opening in which is coaxially disposed a discharge nozzle for liquid. Liquid discharged from the nozzle is adapted to enter the bulb structure through the annular opening surrounding the discharge opening of the nozzle for exiting from the bulb through a suitable outlet.

U.S. Pat. No. 2,908,273 illustrates a nozzle structure, generally similar to those previously described, in combination with power means for supplying liquid to discharge openings in the nozzle structure and withdrawing liquid through outlet openings therein, with such flows being power-actuated.

BRIEF SUMMARY OF THE INVENTION

The present invention is directed to a relatively simple syringe structure which may be readily constructed from metal, plastic, or the like and comprises an elongated nozzle structure which is provided at its proximal end for connection to a liquid supply and at its distal end with a liquid outlet. The structure is also provided with liquid discharge opening therein which, in a preferred embodiment, may be disposed in an intermediate portion of the body relatively close to the distal end and the fluid, the liquid outlet in such end, with such discharge openings communicating, at the proximal end with the exterior so that liquid is free to flow into the discharge openings and the discharge exteriorly from the structure.

In one embodiment of the invention, the structure is designed as an elongated hollow tubular body member provided with the respective liquid outlet and discharge outlet therein and a cooperable stem member having a hollow tubular stem which operatively connects a fluid inlet in the base portion with the fluid outlet at the distal end of the body member. The discharge outlet in the body member communicates with the interior of the hollow body member and the base portion of the stem member is provided with a discharge passageway therein, which operatively connects the interior of the hollow body member with the exterior. Liquid thus may be supplied to the fluid outlet at the distal end of the structure and fluid discharge through the discharge inlet and eventually discharged through the discharge outlet to the exterior.

In another embodiment of the invention, the structure is made in three pieces comprising a body member, a stem member and a base member which is separate from the stem member. In this construction the stem member is secured to the body member by the base member. Again, the hollow stem member forms a connecting passageway from a fluid inlet in the stem member to the fluid outlet in the distal end of the body member with a return discharge passageway extending to the exterior through corresponding discharge inlets disposed in the body member and channels formed in portion of the stem member which communicate at their proximal end with the exterior at the lower end of the base member.

Either embodiments of the invention may be utilized in conjunction with a hollow bell-shaped sealing member of soft rubber or the like, which may be engaged with the structure at the proximal end thereof to provide a fluid seal bettween the syringe structure and the walls of the vaginal orifice.

It will be noted that in either embodiment the liquid outlet and discharge inlet are so disposed in the body member that, in use, they both will be disposed within the vaginal cavity, while the both the fluid inlet and discharge are disposed exteriorly of the vaginal cavity as well as at the exterior side of any sealing member.

Either of the embodiments of the invention illustrated may be constructed from metal or suitable plastic materials. Likewise, the base member and body member in the first embodiment may be constructed to provide a press fit therebetween, or provided with cooperable treads, and in like manner, in the second embodiment, the base member may be connected to the body member by similar connections. In the event the structure is constructed of plastic, the same corresponding parts may be suitably secured by a press fit or by a suitable cementing or welding of the corresponding parts.

BRIEF DESCRIPTION OF THE DRAWINGS

In the drawings wherein like reference characters indicate like or corresponding parts:

FIG. 1 is a side elevational view of syringe structure embodying the present invention;

FIG. 2 is an axial sectional view of the distal portion of the structure illustrated in FIG. 1;

FIG. 3 is a sectional view taken approximately on the line III—III of FIG. 1;

FIG. 4 is an axial sectional view through the proximal end portion of the structure illustrated in FIG. 1, taken approximately on the line IV—IV of FIG. 3;

FIG. 5 is an elevational view similar to FIG. 1 illustrating a modification of the structure illustrated in FIG. 1;

FIG. 6 is an axial sectional view through the proximal end portion of the structure of FIG. 5;

FIG. 7 is a sectional view taken approximately on the line VII—VII of FIG. 5; and FIG. 8 is an axial sectional view taken approximately on the line VIII—VIII of FIG. 7.

DETAILED DESCRIPTION OF THE INVENTION

Referring generally to the drawings and more particularly to FIGS. 1-4, the reference numeral 1 indicates generally an elongated body 1, having a fluid inlet 2 at the proximal end thereof and a plurality of fluid outlets 3 at the distal end thereof which are in communication with the fluid inlet 2, whereby fluid may be supplied to the inlet 2 and discharged through the outlets 3. The body is also provided with a plurality of fluid discharged inlets 4, illustrated as being disposed in an intermediate portion of the body adjacent the distal end of the body 1, which are in communication with discharge outlets 5 at the proximal end of the structure.

As hereinafter described in detail, the inlet 2 and outlet 3 are operatively connected by a passageway and the discharge inlet 4 and discharge outlet 5 are connected by a second passageway, which passageways are independent of one another. FIGS. 2-4 illustrate the details of the construction and in particular the respective fluid passageways therein.

The structure of FIG. 1 may be readily fabricated in the form of two independent members which are suitably assembled to form a unitary structure. The first is the body member 6 which, as illustrated in FIGS. 2-4, is formed with a central bore 7 therein with which the discharge inlets 4 communicate, as clearly illustrated in FIG. 2. Cooperable with the body member 6 is a stem member indicated generally by the numeral 8 and comprising a base member 9 and a hollow stem member 10. As illustrated in FIG. 2 the distal end of the body member 6 is provided with a relatively small coaxial bore 11 therein with which the fluid outlet 3 communicates, with the distal end of the stem 10 extending, with a snug-fit, into said bore 11. The base member 9 is also provided with a concentric portion 12 which is seated in a counter bore 13 formed in a proximal end of the body member 6, with such concentric portion being provided with a plurality of generally rectangularly-shaped channels 14 therein which extend in axial direction and communicate at their upper ends with the bore 7. The lower ends of the channels 14 extend below the proximal end of the body member 6 and form the generally radially extending discharge outlets 5, as clearly illustrated in FIG. 4. As illustrated, the base member 8 may be provided at the fluid inlet 2 with a suitable stem portion 15 adapted to receive a supply hose, or supply syringe ball as partially indicated in broken lines in FIG. 5.

The proximal end of the body member 6 is provided with an annular bead or flange 16 which may form a seat or stop for a sealing member 17 indicated in dotted lines, which may be formed of suitable material such as a relatively soft rubber or the like and is secured to the body member by a press-fit. The member 17 may form a fluid tight seal with the vaginal orifice to prevent liquid flow therefrom other than through the discharge outlets 5.

FIGS. 5-8 illustrate a further embodiment of the invention, which is generally similar to that illustrated in FIG. 1 with the exception that the base member 8 is constructed as a separate component. The base member 8 is secured to the body member 6 and forms the means for securing the stem member 8 to the body member.

In this construction, as illustrated in FIG. 6, the distal end of the body member 6 is provided with an axially extending bore 3a as well as a plurality of radially extending bores with the stem member 10 adapted to supply fluid from the inlet 2 to the fluid outlets 3 as in the construction of FIG. 1. As illustrated in FIGS. 7 and 8, the base member 8 is formed as a separate component with respect to the stem member 10, with the latter having enlarged concentric portion 12 which is provided with three longitudinally extending channels 14 therein, which communicate at their upper end with the bore 7 and at their bottom ends form the discharge outlets 5.

As illustrated in FIG. 8, the base member 8 may be threadedly connected with the adjacent end of the body member 6 or by secured thereto means of a press-fit. Also if desired, where the structure is of plastic or similar material, the parts may be cemented together as well as attached by the use of threads or a press-fit.

In use, the structure such as illustrated in FIG. 1, with the sealing member 17 in position and the fluid inlet 2 suitably connected with a supply means or fluid, the structure is inserted in the vaginal channel and the vaginal orifice sealed by engagement of the sealing member 17 therewith.

In use, the body member 6 is inserted in the vaginal channel and the vaginal orifice sealed by engagement of the sealing member 17 therewith. Following the introduction of the fluid through the outlets 3, such fluid may ultimately enter the discharge inlets 4 and be discharged from the vaginal channel through the discharge outlets 5, exteriorly of the structure.

The structure may be readily cleaned following use, and if constructed in the form of separable components, may be disassembled prior to the cleaning operation.

It will be noted that I have provided an extremely simple yet high efficient structure that is very durable in use.

Although I have described my invention by reference to particular illustrative embodiments, many changes and modifications of the invention may become apparent to those skilled in the art without departing from the spirit and scope of the invention. I therefore intend to include within the patent warranted hereon all such changes and modifications as may reasonably and properly be included within the scope of my contribution to the art.

I claim as my invention:

1. A vaginal syringe device comprising an elongated body of a size to be partially inserted, when in use, in a vaginal canal, said body having at least one fluid outlet in its distal end portion and a fluid inlet in its proximal end portion, said body also having a plurality of spaced fluid discharge inlets therein which are disposed so that the same will be positioned in the vaginal canal when said syringe device is in use, and a plurality of spaced discharge outlets in said proximal end portion, which discharge outlets are so disposed that the same will be positioned exteriorly of such a vaginal canal when in use, said body including two independent passageways therein, one of which connects said fluid inlet and fluid outlet for the flow of liquid from the exterior into such a vaginal canal, and the other of which connects said discharge inlets and said discharge outlets for the flow of liquid from the interior of such a vaginal canal to the exterior thereof, said body comprising a hollow tubular body member one of which forms said distal end portion, a generally coaxial stem member having a bore portion engaged with the proximal end portion of said body member, and an elongated hollow stem portion of a size to be disposed in said tubular body member and extend to and communicate with said fluid outlet in said distal end portion of said body member, said base portion including said fluid inlet therein and said hollow stem portion forming said one passageway connecting said fluid inlet and fluid outlet, said base portion being partially disposed within said body member and including a plurality of longitudinally-extending channels formed in its exterior surface, which channels extend beyond said body member with the exposed portions of said channels forming said discharge outlets.

2. A vaginal syringe device according to claim 1, wherein the interior of said tubular body member surrounding said stem portion forms said second passageway said discharge inlet and outlet communicating with said interior of said body member.

3. A vaginal syringe device according to claim 2, wherein said discharge outlet is disposed, at least in part, in said base portion.

4. A vaginal syringe device according to claim 1, wherein said base portion is in the form of a separate threaded ring-like member, said proximal end of said body member including a threaded portion, said threaded ring-like portion detachably mounted on said threaded portion of said proximal end of said body member and engageable with a portion of said stem member for retaining the same in operative engagement with the body member.

* * * * *